United States Patent [19]

Eisenberg et al.

[11] Patent Number: 5,177,235

[45] Date of Patent: Jan. 5, 1993

[54] SYNTHESIS OF TETRAALKYLSILANES

[75] Inventors: David C. Eisenberg; Gene C. Robinson, both of Baton Rouge, La.

[73] Assignee: Ethyl Corporation, Richmond, Va.

[21] Appl. No.: 897,096

[22] Filed: Jun. 11, 1992

[51] Int. Cl.$^5$ .............................................. C07F 7/08
[52] U.S. Cl. ...................................................... 556/478
[58] Field of Search ........................................... 556/478

[56] References Cited

U.S. PATENT DOCUMENTS

| | | | |
|---|---|---|---|
| 3,927,058 | 12/1975 | Libbey | 556/478 |
| 3,927,059 | 12/1975 | Libbey et al. | 556/478 |
| 3,927,060 | 12/1975 | Libbey | 556/478 |
| 4,367,343 | 1/1983 | Tamborski et al. | 556/478 |
| 4,572,791 | 2/1986 | Onopchenko et al. | 252/46.3 |
| 4,578,497 | 3/1986 | Onopchenko et al. | 556/479 |
| 4,595,777 | 6/1986 | Bakshi et al. | 556/478 |
| 4,650,891 | 3/1987 | Lennon | 556/480 |
| 4,672,135 | 6/1987 | Lennon | 556/480 |
| 4,711,965 | 12/1987 | Nelson | 556/478 |
| 4,711,966 | 12/1987 | Nelson | 556/478 |
| 4,845,260 | 7/1989 | Nelson | 556/478 |
| 4,916,245 | 4/1990 | Nelson | 556/478 |
| 4,946,880 | 8/1990 | Hahn et al. | 556/478 |
| 4,973,724 | 11/1990 | Nelson | 556/465 |
| 4,999,447 | 3/1991 | Nelson | 556/478 |
| 5,124,502 | 6/1992 | Nelson et al. | 556/478 |

Primary Examiner—Paul F. Shaver
Attorney, Agent, or Firm—David E. LaRose

[57] ABSTRACT

This invention relates to a process for preparing tetrahydrocarbylsilane in high yield, comprising: a) forming a reaction mass from molten metal and trihydrocarbylaluminum, in an hydrocarbon solvent under an inert gas atmosphere; b) maintaining the reaction mass at a temperature in the range of from about 100° to about 130° C. for a period of time sufficient to form sodium tetrahydrocarbylaluminate; c) contacting the sodium tetrahydrocarbylaluminate with organotrihalosilane; and d) heating the contacted tetrahydrocarbylaluminate and organotrihalosilane to a temperature and for a period of time sufficient to form the tetrahydrocarbylsilane, wherein the tetrahydrocarbylaluminate and tetrahydrocarbylsilane are formed at a pressure of less than about 3000 KPa and wherein the hydrocarbyl group of the tetrahydrocarbyl silane is one or a mixture of hydrocarbyl groups having less than about 8 carbon atoms each.

27 Claims, No Drawings

SYNTHESIS OF TETRAALKYLSILANES

BACKGROUND

This invention relates to an improved method for preparing tetra-lower-hydrocarbylsilanes in high yield.

Tetrahydrocarbylsilanes are useful in the formulation of hydraulic fluids and lubricants which are stable at high temperatures. Such tetrahydrocarbylsilanes possess excellent viscosities over a wide temperature range, low pour points, and exhibit excellent thermal stabilities. Processes for the preparation of various tetrahydrocarbylsilanes include Tamborski et al., U.S. Pat. No. 4,367,343 which provide a method for preparing tetraalkylsilanes by reacting a halosilicon compound with at least two organometallic compounds.

Onopchenko et al., U.S. Pat. No. 4,578,497 describe a process for the preparation of tetraalkylsilanes by contacting an admixture of at least one alkylsilane and at least one alpha olefin under an inert atmosphere with an oxygenated, platinum-containing catalyst under hydrosilylation conditions. In U.S. Pat. No. 4,572,791, Onopchenko et al. describe a process for preparing a mixture of saturated and unsaturated silahydrocarbons in high yield using a rhodium-containing catalyst in which such admixture contains at least 75 percent saturated silahydrocarbon. In Onopchenko et al. ('791), at least one alpha-olefin containing from 2 to about 20 carbon atoms per molecule and at least one alkylsilane selected from dialkylsilane, trialkylsilane, and mixtures thereof are contacted in the presence of a homogeneous rhodium-containing catalyst having a basicity substantially equal to or less than that provided by a rhodium-containing catalyst having a triphenyl phosphine ligand or a heterogeneous rhodium-containing catalyst.

Tetraalkylsilanes are produced by the process of Bakshi et al., U.S. Pat. No. 4,595,777 wherein a mixture of alkylchlorosilanes and trialkyl aluminum compound are reacted under alkylation conditions, preferably in the presence of an alkali metal salt. The reaction is conducted at a temperature from 150° to 300° C., preferably at elevated pressure of from 1 to about 100 atmospheres under an inert gas such that the more volatile components are kept predominantly in the liquid phase.

Lennon, U.S. Pat. No. 4,650,891 and U.S. Pat. No. 4,672,135 describes methods for preparing tetraorganosilanes by reacting a halo-substituted silane and an organomagnesium compound in the presence of a catalytically effective amount of cyanide or thiocyanate catalyst.

Particularly useful methods for the preparation of tetraalkylsilanes are described in Nelson, U.S. Pat. No. 4,711,965; U.S. Pat. No. 4,711,966; U.S. Pat. No. 4,845,260; U.S. Pat. No. 4,916,245; U.S. Pat. No. 4,973,724; and U.S. Pat. No. 4,999,447. U.S. Pat. No. 4,711,965 describes a process wherein an alkali metal aluminum tetraalkyl is reacted with an alkyl trihalosilane. U.S. Pat. No. 4,711,966 relates to the preparation of tetraalkylsilanes by reacting a trialkylaluminum and an alkali metal aluminum tetraalkyl with a silicon tetrahalide in a certain mole ratio. U.S. Pat. No. 4,845,260; and U.S. Pat. No. 4,973,724 relate to a three step process for the preparation of tetraalkylsilanes by reacting Na, Al, H₂, and olefin in the presence of an organoaluminum catalyst to prepare an intermediate product, which can be reacted with a trihaloalkyl-silane to produce the desired product. U.S. Pat. No. 4,916,245 and U.S. Pat. No. 4,999,447 describe the preparation of tetraalkylsilanes by reacting an alkali metal aluminum tetraalkyl and an olefin with an alkyl trihalosilane.

Beard, U.S. Pat. No. 3,291,742, describes certain aryl aliphatic-oxy silanes which are useful as heat transfer media, hydraulic fluids, or lubricants, and which are stable liquids over a wide temperature range. In the process for preparing such aryl aliphatic-oxy silanes, an arylhalosilane is reacted with an appropriate alcohol. Other hydrocarbyl-oxy silanes are described in Askey et al., U.S. Pat. No. 4,141,851, and Ando et al., U.S. Pat. No. 5,039,555.

While the above processes are useful in preparing a variety of tetrahydrocarbylsilanes, there remains a need for an improved process preparing tetra-lower-hydrocarbylsilanes in high yields at more moderate pressures. The use of more moderate pressures greatly decreases the cost of the reactor and provides less operating difficulties.

THE INVENTION

This invention provides, for the first time, a process for preparing lower tetrahydrocarbylsilanes at moderate pressures and in high yield from alkali metal tetrahydrocarbylaluminate. In one embodiment, this invention relates to a process for preparing tetrahydrocarbylsilane in high yield, comprising: a) forming a reaction mass from molten alkali metal and trihydrocarbyl aluminum, in an hydrocarbon solvent under an inert gas atmosphere; b) maintaining the reaction mass at a temperature in the range of from about 100° to about 130° C. for a period of time sufficient to form alkali metal tetrahydrocarbylaluminate; c) contacting the alkali metal tetrahydrocarbylaluminate with organotrihalosilane; and d) heating the contacted tetrahydrocarbylaluminate and organotrihalosilane to a temperature and for a period of time sufficient to form the tetrahydrocarbylsilane wherein the alkali metal tetrahydrocarbylaluminate and tetrahydrocarbylsilane are formed at a pressure of less than about 3000 KPa and wherein the hydrocarbyl group of the tetrahydrocarbylsilane is one or a mixture of hydrocarbyl groups having less than about 8 carbon atoms each.

Until now, when preparing tetrhydrocarbylsilane from alkali metal tetrahydrocarbylaluminate wherein the hydrocarbyl groups contain less than about 8 carbon atoms, high pressure reaction equipment was required, especially for alkali metal tetrahydrocarbylaluminate reaction step. By high pressure is meant superatmopsheric pressures in excess of about 1500 KPa (about 200 pounds per square inch). Typically, pressures in excess of 3000 to 7000 KPa were encountered with low molecular weight reactants in order to achieve high yields of product. A method has now been discovered which can achieve high yields of product at moderate pressures. By high yields is meant greater than about 40% yield based on the theoretical yield.

In another embodiment, this invention provides an improvement in a process for preparing a tetrahydrocarbylsilane of the formula

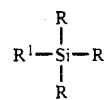

wherein each of R and R¹ is a hydrocarbyl group having less than 8 carbon atoms, the process comprising: a)

forming a reaction mass of molten alkali metal and a hydrocarbon solvent at a temperature of from about 100° to about 130° C.; b) charging R₃Al to the reaction mass while maintaining the reaction mass under an inert gas atmosphere; c) cooling the reaction mass to a temperature within the range of 20° to 100° C., preferably about 40° to about 70° C.; d) feeding R¹SiCl₃ to the cooled reaction mass; and e) subsequently, heating the reaction mass to a temperature above about 100° C. for a period of time sufficient to form the tetrahydrocarbylsilane, wherein the pressure during the reaction is less than about 3000 KPa.

The tetrahydrocarbylsilanes produced by the process of this invention may be represented by the formula

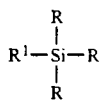

wherein each of R and R¹ is the same or different and is a hydrocarbyl group having less than 10 carbon atoms. It is preferred that each R be the same. More preferably each R is an alkyl group having less than about 6 carbon atoms, and most preferably, R is an n-butyl group. R¹ may be selected from an alkyl, aryl, alkyaryl, or aralkyl group having less than 10 carbon atoms. Preferably, R¹ is an alkyl or aryl group, and most preferably, R¹ is selected from the group consisting essentially of methyl, ethyl, propyl, or phenyl. Preferred products formed by the process of this invention include, methyltri-n-butylsilane, methyltriethylsilane, ethyltri-n-butylsilane, ethyltripropylsilane, phenyltri-n-butylsilane, phenyltriethylsilane or mixtures thereof. Particularly preferred products are methyltri-n-butylsilane, phenyltri-n-butylsilane, and methyltriethylsilane.

Initially, the reaction vessel is charged with alkali metal and an inert hydrocarbon solvent, more preferably, an aliphatic hydrocarbon solvent, and most preferably, the solvent is selected from n-hexane, n-heptane, isooctane, and n-octane. Other inert organic solvents may also be used provided they are in the liquid phase under the reaction conditions.

A key feature of this invention is the use of a molten alkali metal as a reactant to form an intermediate alkali metal tetrahydrocarbylaluminate reactant. While any number of alkali metals may be used to form metal tetrahydrocarbylaluminates, higher temperatures are usually required for alkali metals having a melting point much above that of sodium. Thus the preferred alkali metals are sodium, potassium, and alloys of sodium and potassium. It is understood of course, that such alloys of sodium and potassium may also contain other elements such as lithium, provided the melting point of the alloy is not much above the melting point of sodium. Suitable sodium-potassium alloys may contain from 0 to about 25 weight percent potassium, preferably less than about 10 weight percent potassium, and most preferably from 0 to about 5 weight percent potassium. It is highly preferred that the sodium alloy contain less than about 5 weight percent lithium.

In the preferred embodiments of this invention, the temperature of reaction for forming the sodium tetrahydrocarbylaluminate does not exceed about 150° C. Preferably, the temperature is less than about 140° C., and most preferably is in the range of from about 100° C. to about 130° C. At a temperature of lower than about 100° C., the alkali metal may be in a solid form rather than in molten form which is preferred.

The ratio of alkali metal to trihydrocarbylaluminum in the reaction vessel is typically in the range of from about 12 gram atoms of sodium per mole of trihydrocarbylaluminum to about 25 gram atoms of sodium per mole of trihydrocarbylaluminum. Preferably the ratio of moles of sodium to moles of trihydrocarbylaluminum is in the range of from about 0.65:1 to about 0.8:1 and most preferably from about 0.7:1 to about 0.75:1.

During the formation of the intermediate alkali metal tetrahydrocarbylaluminate an inert gas atmosphere is maintained in the reaction vessel. Inert gases which may be used include, nitrogen, argon, and the noble gases.

Once the reaction vessel is charged with solvent and alkali metal, the solvent and alkali metal are heated to form molten alkali metal. Once the alkali metal is in the molten form, the trihydrocarbylaluminum reactant is fed to the reaction vessel to form a reaction mass. During the feeding of the trihydrocarbylaluminum reactant, the reaction mass is agitated or stirred while maintaining the reaction temperature preferably in the range of from about 100° to about 130° C. When all of the trihydrocarbylaluminum reactant has been fed to the reaction vessel, the reaction mass thus formed is held for a period of time to assure sufficient contact of the reactants. This period of time may range from 5 minutes to 5 hours or more depending on the scale of the reaction and the rate of agitation.

Subsequent to the hold period, the reaction mass is cooled to less than about 100° C., preferably less than about 80° C. and most preferably to a temperature in the range of from about 40° to about 70° C. Once the reaction mass is cooled, any free aluminum metal may be removed from the reaction mass by decanting the liquid, filtration, and the like. It is not necessary, however to remove free aluminum which may remain in the reaction mass prior to the next step in the reaction.

The sodium tetrahydrocarbylaluminate thus formed is then contacted with an amount of organotrihalosilane sufficient to form, in high yield, the tetrahydrocarbylsilane product. The organotrihalosilane may be represented by the formula R¹SiX₃ wherein R¹ is an aryl, alkyl, cycloalkyl, alkylaryl, or aralkyl group. The three groups indicated by X are halide radicals; preferably all three are the same; however, reactants with two or three halo groups per molecule can be used. More preferably, the halide groups are chloro or bromo radicals, most preferably they are all chloro groups. In a preferred embodiment, the organotrihalosilane is an organotrichlorosilane, more preferably methyltrichlorosilane, ethyltrichlorosilane, propyltrichlorosilane, or phenyltrichlorosilane.

The amount of organotrihalosilane contacted with the alkali metal tetrahydrocarbylaluminate is in the range of from about 0.5 to 1.5 moles of organotrihalosilane per mole of alkali metal tetrahydrocarbylaluminate. A more preferred range is from about 0.85 to about 1.3 moles of organotrihalosilane per mole of alkali metal tetrahydrocarbylaluminate, and most preferably from about 1.0 to about 1.15 moles of organotrihalosilane per mole of alkali metal trihydrocarbylaluminate. It is desirable to use less than a stoichiometric amount of organotrihalosilane in the second stage of the reaction to assure that no Si-Cl bonds remain upon completion of the reaction step.

When adding the organotrihalosilane to the reaction vessel, it is desirable to maintain the reactor pressure at about atmospheric pressure. If the pressure should rise to superatmospheric, the reactor can be vented to maintain about atmospheric pressure.

Once all of the organotrihalosilane has been fed to the reactor, it is desirable to agitate the reactor contents for a period of time to assure intimate contact among the reactants. Depending on the scale of the reaction, this period of time can vary between 5 minutes and 5 hours or more.

Subsequent to the period of time after feeding the organotrihalosilane to the reactor, the reactor is sealed and the reactor contents are heated under controlled heating conditions to a temperature above about 120° C. Preferred temperatures range from about 130° C. to about 200° C. and most preferably from about 150° C. to about 185° C. This temperature is desirably maintained for a period of time sufficient to assure substantially complete reaction. Such period of time may range from 1 hour to 48 hours or more, again depending on the scale of the reaction. At the lower temperatures, within the preferred range, the reaction time may be longer than with higher temperatures, however, good yields of product are obtained at a lower pressure with temperatures within the desired range.

After forming the tetrahydrocarbylsilane by the foregoing method, the reaction mass is allowed to cool slowly while agitating the reaction mass. Purification and separation of the product from the reaction mass is achieved by feeding the reaction mass to a sufficient amount of aqueous base with agitation under an inert gas atmosphere. During the neutralization, two phases are formed, an aqueous phase and an organic phase. The organic phase containing the product can then be separated from the aqueous phase. Aqueous bases which may be used include NaOH, KOH, $Ca(OH)_2$, $Mg(OH)_2$, $Ba(OH)_2$, or the like.

The following example is given to illustrate the invention and is not intended to limit the scope of the invention.

EXAMPLE 1

Preparation of Methyltributylsilane

In a 300 mL medium pressure reactor, tri-n-butylaluminum (90 grams, 0.45 mol) are added to 7-8 grams (0.3-0.35 mols) of molten sodium and 20-40 mL of n-octane which are maintained at a temperature of 100°-120° C. under a nitrogen pressure atmosphere. After all of the tri-n-butylaluminum has been added to the reaction vessel, the mixture is stirred for 15 minutes to 1 hour. The reaction vessel is then cooled to 45° C. to 65° C. and 56-63 grams (0.37-0.42 mols) of methyl trichlorosilane are added dropwise to the stirred reaction mass. The resulting mixture is then agitated for 15 minutes to 1 hour and the pressure is maintained at about atmospheric pressure by venting the reactor. Subsequent to the agitation period, the reactor is sealed and heated to about 100° C., and again vented if desired to reduce the pressure. The contents of the reactor are then heated slowly to 120° C. to 135° C. and held in this temperature range for 1 to 1.5 hours. In the next temperature sequence, the reactor contents are heated to 150° C. to 185° C. and held in this temperature range for 5 to 48 hours. During the hold period the pressure in the reactor ranges from 70 psi (480 KPa) at the lower temperature to about 200 psi (1379 KPa) at the higher temperature. At the end of the hold period, the reactor contents are allowed to cool slowly while agitating the reactor contents. Once cooled, the reaction mixture is added, with stirring to 200 to 700 mL of 10 to 20 wt. % NaOH while maintaining a nitrogen atmosphere in the reaction vessel. An organic layer containing the product and an aqueous layer are formed. The organic layer is separated from the aqueous layer and washed with salt water. Isolation of the washed product may be obtained by vacuum distillation. Yield of methyltributyl-silane by the foregoing method is in the range of 40 to 70% based on theoretical.

EXAMPLE 2

Preparation of Methyltriethylsilane

Methyltriethylsilane is prepared by the general procedure of Example 1 using triethylaluminum and methyltrichlorosilane.

EXAMPLE 3

Preparation of Phenyltri-n-butylsilane

Phenyltributylsilane is prepared by the general procedure of Example 1 using tri-n-butylaluminum and phenyltrichlorosilane.

The tetrahydrocarbylsilane compositions of this invention may be used neat in cooling fluid applications or may be admixed with other ingredients such as antioxidants, anti-wear agents, metal passivators, corrosion inhibitors, carrier oils, and the like. The preparation of such mixtures is well known by those skilled in the art. The amount and proportion of other ingredients should be sufficient to provide the desired properties while not adversely affecting the performance characteristics of the tetrahydrocarbylsilane predominant composition. Thus the tetrahydrocarbylsilane predominant composition may comprise about 75 to about 100 weight percent of the total formulated product and preferably about 90 to about 100 weight percent of the total formulation.

Suitable antioxidants used in tetrahydrocarbylsilane formulations are those which are soluble in the tetrahydrocarbylsilane product including phenolic antioxidants, aromatic amine antioxidants, sulfurized phenolic antioxidants, alkyl, dialkyl and alkylated diphenyl amines, thioester phenolic antioxidants, as well as boronated phenols and boronated sulfurized phenols.

Of the suitable antioxidants, the alkylated diphenyl-amines are preferred. Examples of such diphenylamines include $C_4$-$C_{27}$ alkylated diphenyl amines, e.g. 3,3'-butyl-diphenylamine, 3,3'-tert-butyl-diphenylamine, 3,3'-octyl-diphenylamine, 3,3'- nonyl-diphenylamine, 3,3'-dodecyl-diphenylamine, 3,3'-hexadecyldiphenylamine, 3,3'-octadecyl-diphenylamine, 4,4'-butyl-diphenylamine, 4,4'-tert-butyl-diphenylamine, 4,4'-octyl-diphenylamine, 4,4'-nonyl-diphenylamine, 4,4'-dodecyl-diphenylamine, 4,4'-hexadecyl-diphenylamine, 4,4'-octadecyl-diphenylamine, 4,4'heptacosyl-diphenylamine phenyl-naphthylamine, N,N'-di-butyl-p-phenylenediamine, and/or mixtures thereof. Particularly preferred are mixtures of $C_4$, $C_8$, $C_{12}$, $C_{16}$ alkylated diphenylamines and $C_9$, $C_{18}$, $C_{27}$ alkylated diphenyl-amines.

Other antioxidant compounds useful in tetrahydrocarbylsilane formulations include phenolic antioxidants, preferably the bis(di-alkylphenols), sulfurized bis(di-alkylphenols), and borated alkylated phenols. Particularly preferred are the alkylene bis(di-tert-butyl-phenols) and sulfurized alkylene bis(di-tert-butyl-phenols). Examples of suitable alkylene bis(di-tert-butylphenols) are 4,4'-methylene-bis-(2,6-di-tert-butylphenol), 4,4'-ethylene-bis-(2,6-di-tert-butylphenol), 4,4'-propylene-bis-(2,6-di-tert-butylphenol), and 4,4'-isopropylene-bis-(2,6-di-tert-butylphenol). 2,6-di-tert-butyl-p-cresol, 4,4'-bis-(2,6-diisopropylphenol), 2,2'-thio-bis-(4-methyl-6-tert-butylphenol), and mixtures thereof. The sulfurized alkylphenols include, 3,3'-butyl-diphenylsulfide, 3,3'-tert-butyl-diphenylsulfide, 3,3'-octyl-diphenylsulfide, 3,3'-nonyl-diphenylsulfide, 3,3'-dodecyl-diphenylsulfide, 3,3'-hexadecyl-diphenylsulfide, 3,3'-octadecyl-diphenylsulfide, 4,4'-butyl-diphenylsulfide, 4,4'-tert-butyl-diphenylsulfide, 4,4'-octyl-dephenylsulfide, 4,4'-nonyl-diphenylsulfide, 4,4'-dodecyl-diphenylsulfide, 4,4'-hexadecyl-diphenylsulfide, 4,4'-octadecyl-diphenylsulfide, 4,4'-heptacosyl-diphenylsulfide, and/or mixtures thereof.

Still other useful antioxidants include thio-bis(hydroxyhydrocinannamates), e.g. thiodiethylene bis(3,5-di-tert-butyl-4-hydroxyhydrocynannamate), and thiopropylene bis(3,5-di-tert-butyl-4-hydroxyhydrocynannamate) and/or mixtures thereof.

Formulations containing the tetrahydrcarbylsilanes of this invention may also include suitable anti-wear agents which are soluble in the silahydrocarbon base fluids such as hydrocarbyl phosphates, hydrocarbyl phosphites, or hydrocarbyl fluorophosphites. Preferred anti-wear agents include tricresylphosphate (TCP), zinc dialkyldithiophosphate (ZDDP), dibutyl hydrogen phosphite, trinonyl phosphite, triphenyl phosphite, dioleyl hydrogen phosphite, and resorcinol bis(nonylphenyl)phosphate with zinc dialkyldithiophosphate (ZDDP) being the most preferred. It is to be understood that while some compounds are classified as anti-oxidants and others as anti-wear agents, in some formulations contemplated by this invention, the same compound may perform both functions. For example, ZDDP may be used as both an antioxidant and an anti-wear agent in combination with certain polyalphaolefins.

Other ingredients such as metal passivators and corrosion inhibitors may also be used with the compositions and formulations of this invention. Metal passivators useful with this invention include thiazoles, triazoles and thiadiazoles such as benzotria-zole, 2-mercaptobenzotriazole, 2,5-dimercaptothiadiazole; and salts of salicylaminoguaanidine, quinizarin, propylgallate, and the like.

Useful rust/corrosion inhibitors include primary, secondary or tertiary aliphatic or cycloaliphatic amines and amine salts of organic and inorganic acids; oil-soluble alkylammonium carboxylates; substituted imidazolines and oxazolines; alkali metal and alkaline earth metal carbonates; alkali metal and alkaline earth metal salts of alkylbenzene sulfonic acids, such as barium dinonylnaphthalenesulfonates, calcium petroleum sulfonates, and the like; esters, anhydrides, and metals salts of organic acids, such as sorbitan monooleate, lead naphthenate, and dodecylsuccinic anhydride; and the like. Use can also be made of dimer and trimer acids, such as are produced from tall oil fatty acids, oleic acid, linoleic acid, or the like. Products of this type are currently available from various commercial sources, such as, for example, the dimer and trimer acids sold under the HYSTRENE trademark by the Humco Chemical Division of WitcoChemical Corporation and under the EMPOL trademark by Emery Chemicals. Other corrosion inhibitor for use in the practice of this invention are the alkenyl succinic acid and alkenyl succinic anhydride corrosion inhibitors such as, for example, tetrapropenylsuccinic acid, tetradecenylsuccinic anhydride, hexadecenylsuccinic acid, hexadecenylsuccinic anhydride, and the like.

Variations of the invention are within the spirit and scope of the appended claims.

What is claimed is:

1. A process for preparing tetrahydrocarbylsilane, in high yield, comprising:
   a) forming a reaction mass from molten alkali metal and trihydrocarbyl aluminum, in an hydrocarbon solvent under an inert gas atmosphere;
   b) maintaining the reaction mass at a temperature in the range of from about 100° to about 130° C. for a period of time sufficient to form alkali metal tetrahydrocarbylaluminate;
   c) contacting the alkali metal tetrahydrocarbylaluminate with organotrihalosilane; and
   d) heating the contacted tetrahydrocarbylaluminate and organotrihalosilane to a temperature and for a period of time sufficient to form the tetrahydrocarbylsilane wherein the alkali metal tetrahydrocarbylaluminate and tetrahydrocarbylsilane are formed at a pressure of less than about 3000 KPa and wherein each hydrocarbyl group of the tetrahydrocarbylsilane is one or a mixture of hydrocarbyl groups having less than about 8 carbon atoms.

2. The process of claim 1 wherein the molten alkali metal is sodium.

3. The process of claim 1 wherein the molten alkali metal is a sodium-potassium alloy.

4. The process of claim 1 wherein the molten alkali metal is a sodium-potassium alloy containing from 0 to about 5 weight percent potassium.

5. The process of claim 1 wherein the trihydrocarbyl aluminum is tri-n-butyl aluminum.

6. The process of claim 1 wherein the hydrocarbon solvent is n-octane.

7. The process of claim 1 wherein the organotrihalosilane is methyltrichlorosilane.

8. The process of claim 1 wherein the organotrihalosilane is phenyltrichlorosilane.

9. The process of claim 1 wherein the tetrahydrocarbyl-silane is methyl-tri-n-butylsilane.

10. The process of claim 1 wherein the tetrahydrocarbyl-silane is phenyl-tri-n-butylsilane.

11. The process of claim 1 wherein the tetrahydrocarbylsilane formation pressure is less than about 2000 KPa.

12. An improvement in a process for preparing a tetrahydrocarbylsilane of the formula

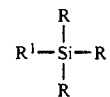

wherein each of R and R$^1$ is a hydrocarbyl group having less than 8 carbon atoms, the process comprising:
   a) forming a reaction mass of molten alkali metal and a hydrocarbon solvent at a temperature of from about 100° to about 130° C.;
   b) charging R$_3$Al to the reaction mass while maintaining the reaction mass under an inert gas atmosphere;
   c) cooling the reaction mass to a temperature within the range of 20° to 100° C;

d) feeding $R^1SiCl_3$ to the cooled reaction mass; and e) subsequently, heating the reaction mass to a temperature above about 100° C. for a period of time sufficient to form the tetrahydrocarbylsilane wherein the pressure during the reaction is less than about 3000 kPa.

13. The process of claim 12 wherein R is a $C_1$ to $C_5$ alkyl group.

14. The process of claim 12 wherein $R_3Al$ is tri-n-butyl aluminum.

15. The process of claim 1 wherein the molten alkali metal is sodium.

16. The process of claim 1 wherein the molten alkali metal is a sodium-potassium alloy.

17. The process of claim 1 wherein the molten alkali metal is a sodium-potassium alloy containing from 0 to about 5 weight percent potassium.

18. The process of claim 12 wherein $R^1$ is a $C_1$ to $C_6$ alkyl or an aryl group.

19. The process of claim 12 wherein $R^1$ is a methyl group.

20. The process of claim 12 wherein $R^1$ is a phenyl group.

21. The process of claim 12 wherein $R^1$ is a methyl group and each or R is an n-butyl group.

22. The process of claim 12 $R^1$ is a phenyl group and each or R is an n-butyl group.

23. The process of claim 12 wherein the tetrahydrocarbylsilane formation pressure is less than about 2000 KPa.

24. A process for preparing organotri-n-butylsilane in high yield, comprising:

a) forming a reaction mass from molten sodium and tri-n-butyl aluminum, in an hydrocarbon solvent under an nitrogen atmosphere;

b) maintaining the reaction mass at a temperature in the range of from about 100° to about 130° C. for a period of time sufficient to form sodium tetra-n-butylaluminate;

c) contacting the sodium tetra-n-butylaluminate with $R^1SiCl_3$; and d) heating the contacted tetra-n-butylaluminate and $R^1SiCl_3$ to a temperature and for a period of time sufficient to form the organotri-n-butylsilane wherein the tetra-n-butylaluminate and organotri-n-butylsilane are formed at a pressure of less than about 3000 KPa.

25. The process of claim 24 wherein $R^1$ is a methyl group.

26. The process of claim 24 wherein $R^1$ is a phenyl group.

27. The process of claim 25 wherein the organotri-n-butylsilane formation pressure is less than about 2000 KPa.

* * * * *